US010092761B2

United States Patent
An et al.

(10) Patent No.: US 10,092,761 B2
(45) Date of Patent: Oct. 9, 2018

(54) AUTOMATIC VECTOR SELECTION FOR MULTI-SITE PACING

(71) Applicant: Cardiac Pacemakers, Inc., St. Paul, MN (US)

(72) Inventors: Qi An, Blaine, MN (US); Yinghong Yu, Shoreview, MN (US); Pramodsingh Hirasingh Thakur, Woodbury, MN (US); David L. Perschbacher, Coon Rapids, MN (US); Jason Humphrey, New Brighton, MN (US); Yi Zhang, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 39 days.

(21) Appl. No.: 15/187,252

(22) Filed: Jun. 20, 2016

(65) Prior Publication Data
US 2017/0001011 A1   Jan. 5, 2017

Related U.S. Application Data

(60) Provisional application No. 62/187,534, filed on Jul. 1, 2015.

(51) Int. Cl.
*A61N 1/00* (2006.01)
*A61N 1/368* (2006.01)
(Continued)

(52) U.S. Cl.
CPC ......... *A61N 1/3684* (2013.01); *A61N 1/3627* (2013.01); *A61N 1/36514* (2013.01);
(Continued)

(58) Field of Classification Search
CPC .............. A61N 1/3627; A61N 1/36514; A61N 1/3684; A61N 1/3708; A61N 1/371; A61N 1/37247
See application file for complete search history.

(56) References Cited

U.S. PATENT DOCUMENTS

| | | | |
|---|---|---|---|
| 4,763,646 A | | 8/1988 | Lekholm |
| 4,980,379 A | * | 12/1990 | Belardinelli ........... A61K 31/00 514/259.1 |

(Continued)

FOREIGN PATENT DOCUMENTS

| | | |
|---|---|---|
| WO | WO-2012087760 A1 | 6/2012 |
| WO | WO-2016061366 A1 | 4/2016 |

OTHER PUBLICATIONS

"U.S. Appl. No. 14/884,417, Advisory Action dated Jun. 7, 2017", 6 pgs.

(Continued)

*Primary Examiner* — George Manuel
(74) *Attorney, Agent, or Firm* — Schwegman Lunderg & Woessner, P.A.

(57) ABSTRACT

Systems and methods for evaluating multiple candidate electrostimulation vectors for use in therapeutic cardiac stimulation are disclosed. The system can include a programmable electrostimulator circuit for delivering electrostimulation to one or more sites of a heart according to multiple candidate electrostimulation vectors. One or more physiologic sensors can detect resulting physiologic responses to the electrostimulation. A processor circuit can generate categories of indicators including therapy efficacy indicators, battery longevity indicators, or complication indicators using the sensed physiologic responses. The candidate electrostimulation vectors can be ranked according to the categories of indicators in specified orders. The system can include a user interface for displaying the ranked candidate electrostimulation vectors, and allowing the user to select one or more electrostimulation vectors and programming the electrostimulator circuit to deliver therapeutic electrostimulation to at least one site of the heart using the selected electrostimulation vectors.

20 Claims, 5 Drawing Sheets

(51) Int. Cl.
  *A61N 1/362* (2006.01)
  *A61N 1/37* (2006.01)
  *A61N 1/372* (2006.01)
  *A61N 1/365* (2006.01)

(52) U.S. Cl.
  CPC ........... *A61N 1/371* (2013.01); *A61N 1/3708* (2013.01); *A61N 1/37247* (2013.01)

(56) References Cited

U.S. PATENT DOCUMENTS

| | | |
|---|---|---|
| 6,772,008 B2 | 8/2004 | Zhu et al. |
| 7,392,085 B2 | 6/2008 | Warren et al. |
| 7,620,452 B1 | 11/2009 | Russie |
| 7,853,327 B2 | 12/2010 | Patangay et al. |
| 8,055,343 B2 | 11/2011 | Gandhi et al. |
| 8,509,890 B2 | 8/2013 | Keel et al. |
| 8,527,049 B2 | 9/2013 | Koh et al. |
| 8,666,490 B1 | 3/2014 | Ryu |
| 8,886,313 B2 | 11/2014 | Siejko et al. |
| 8,972,228 B2* | 3/2015 | Ghosh .................. A61B 5/0402 600/374 |
| 2003/0083710 A1 | 5/2003 | Ternes et al. |
| 2003/0083711 A1 | 5/2003 | Yonce et al. |
| 2005/0137638 A1 | 6/2005 | Yonce et al. |
| 2009/0030334 A1 | 1/2009 | Anderson et al. |
| 2009/0043351 A1 | 2/2009 | Sathaye et al. |
| 2010/0042174 A1 | 2/2010 | Koh et al. |
| 2012/0078320 A1 | 3/2012 | Schotzko et al. |
| 2012/0101546 A1* | 4/2012 | Stadler .................. A61N 1/3708 607/28 |
| 2012/0191154 A1 | 7/2012 | Ryu et al. |
| 2013/0030484 A1 | 1/2013 | Zhang et al. |
| 2013/0184777 A1 | 7/2013 | Hellman et al. |
| 2013/0289640 A1 | 10/2013 | Zhang et al. |
| 2013/0289641 A1 | 10/2013 | Gustafsson et al. |
| 2013/0296962 A1 | 11/2013 | Keel et al. |
| 2014/0277243 A1 | 9/2014 | Maskara et al. |
| 2015/0165204 A1* | 6/2015 | Yu ..................... A61N 1/37247 607/18 |
| 2015/0165212 A1* | 6/2015 | Saha ..................... A61N 1/371 607/28 |
| 2016/0106987 A1 | 4/2016 | An et al. |
| 2016/0206887 A1 | 7/2016 | Maskara et al. |

OTHER PUBLICATIONS

"U.S. Appl. No. 14/884,417, Final Office Action dated Mar. 23, 2017", 19 pgs.

"U.S. Appl. No. 14/884,417, Non Final Office Action dated Sep. 27, 2016", 14 pgs.

"U.S. Appl. No. 14/884,417, Non Final Office Action dated Sep. 29, 2017", 16 pgs.

"U.S. Appl. No. 14/884,417, Response filed May 23, 2017 to Final Office Action dated Mar. 23, 2017", 19 pgs.

"U.S. Appl. No. 14/884,417, Response filed Dec. 27, 2016 to Non Final Office Action dated Sep. 27, 2016", 18 pgs.

"U.S. Appl. No. 14/884,417, Response filed Dec. 26, 2017 to Non Final Office Action dated Sep. 29, 2017", 15 pgs.

"International Application Serial No. PCT/US2015/055762, International Search Report dated Jan. 12, 2016", 6 pgs.

"International Application Serial No. PCT/US2015/055762, Written Opinion dated Jan. 12, 2016", 7 pgs.

Asbach, Stefan, et al., "Vector Selection of a Quadripolar Left Ventricular Pacing Lead Affects Acute Hemodynamic Response to Cardiac Resynchronization Therapy: A Randomized Cross-Over Trial", Plos One; vol. 8; Issue 6, (Jun. 2013), 1-6.

Pappone, Carlo, et al., "Cardiac Resynchronization Therapy with Multisite Left Ventricular Pacing Improves Acute Hemodynamic Response in Patients", Abstract 13412; 2012 AHA, (2012), 1-2.

* cited by examiner

AUTOMATIC VECTOR SELECTION FOR MULTI-SITE PACING

CLAIM OF PRIORITY

This application claims the benefit of priority under 35 U.S.C. § 119(e) of U.S. Provisional Patent Application Ser. No. 62/187,534, filed on Jul. 1, 2015, which is herein incorporated by reference in its entirety.

TECHNICAL FIELD

This document relates generally to medical devices, and more particularly, to devices and methods for evaluating electrostimulation vectors used for therapeutic stimulation of a heart.

BACKGROUND

Congestive heart failure (CHF) is a leading cause of death in the United States. CHF occurs when the heart is unable to adequately supply enough blood to maintain a healthy physiological state. CHF can be treated by drug therapy, or by an implantable medical device (IMD) such as for providing cardiac electrostimulation therapies, including resynchronization therapy (CRT) to correct cardiac dyssynchrony within a ventricle or between ventricles.

The IMD can chronically stimulate excitable tissues or organs, such as a heart, to treat abnormal cardiac rhythms or to help improve cardiac performance in a patient with CHF. Such ambulatory medical devices can have at least first and second electrodes that can be positioned within the heart or on a surface of the heart for contacting the cardiac tissue. The electrodes can be electrically coupled to an electronics unit such as a pulse generator, such as via a lead, and can be used to deliver one or more electrostimulations to the heart, such as to restore or to improve the normal heart function.

Overview

Cardiac stimulation using an implantable medical device (IMD) can involve one or more implantable leads that can be transvascularly inserted into one of the heart chambers, such as an atrium or a ventricle. Stimulation of the heart can be accomplished through direct myocardium stimulation using at least two electrodes that can be electrically connected to the IMD and in close contact with the cardiac tissue. The two electrodes constitute an electrostimulation vector. The electrodes can be positioned along the one or more implantable leads or catheters, or located at an untethered implantable pacing unit. The stimulation can be provided at specified stimulation strength (e.g., stimulation energy) sufficient to capture the heart tissue, that is, the stimulation can effectively cause depolarization propagating to a part or the entirety of the heart.

During the CRT therapy, synchronized stimulation can be applied to the left ventricle (LV) and the right ventricle (RV) of a heart. Conventionally, there can be one RV pacing site and one LV electrostimulation site. Stimulation of multiple sites on a chamber of the heart (such as pacing at multiple LV sites), generally known as multi-site pacing, has been proposed as an alternative to the conventional single site CHF therapy. Multi-site pacing can involve electrostimulation delivered at two or more sites in at least one heart chamber (such as LV) within a cardiac cycle, such as simultaneous stimulation or separated by a specified temporal offset less than a sensed or paced time interval value of the cardiac cycle. Multiple electrodes distributed on at least one of heart chamber can be used to constitute electrostimulation vectors for multi-site pacing. Clinicians can choose from the candidate pacing vectors one or more pacing vectors for multi-site pacing to restore or improve a patient's cardiac function. Compared to the CRT therapy with single site LV electrostimulation, multi-site LV electrostimulation can more significantly improve cardiac hemodynamic outcome, and therefore be more beneficial to some patients at least due to its more effective recruitment of excitable cardiac tissues.

Despite their therapeutic advantage over the conventional CRT therapy in certain patients with cardiac diseases, multi-site pacing can involve increased complexity in both system design and operation. Assessment of the candidate pacing sites or pacing vectors generally involves evaluating a number of clinical factors and device parameters, including patient's acute and chronic hemodynamic response, therapy efficacy, undesirable effects such as phrenic nerve activation, power consumption and its effect on the device longevity, among others. To determine an "optimal" electrostimulation scheme such as a configuration of a pacing vector, clinicians generally need to run a series of tests using multiple candidate pacing vectors that involve various electrode combinations, and compare the respective performances corresponding to the candidate pacing vectors. With more electrodes become available (such as a multi-electrode implantable lead or catheter) for use in multi-site pacing, there is a larger pool of candidate electrostimulation vectors. Identifying patients that are more likely to benefit from multi-site pacing and selecting "optimal" pacing sites or pacing vectors can be both clinically challenging and time consuming than selecting a single pacing site for conventional CRT therapy. Additionally, effective pacing sites can be affected by a variety of factors including lead or electrode positioning at the heart, configurations of the pacing vector, stimulation parameters, pathophysiology of the heart such as myocardial infarction, growth of fibrous tissue or scar tissue around the electrode, lead integrity, and progression of cardiac disease or change in health condition, among others. As a result, a previously identified pacing site or a pacing vector may not provide desired or adequate electrostimulation therapy in the patient. The present inventors have recognized, among other things, that there remains a demand for systems and methods that can provide a more efficient process of evaluating the electrostimulation vectors, and identifying one or more vectors for therapeutic cardiac stimulation, such as CRT therapy or multisite pacing, to improve patient outcome.

This document discusses, among other things, a system for evaluating a plurality of candidate electrostimulation vectors for use in therapeutic stimulation of a heart. The system can include an electrostimulator circuit for delivering electrostimulation to one or more sites of a heart according to multiple candidate electrostimulation vectors, and one or more physiologic sensors for detecting resulting physiologic responses to electrostimulation. The system can rank the candidate electrostimulation vectors based on therapy efficacy indicators and battery longevity indicators produced from the sensed physiologic responses. The system can present the ranked candidate electrostimulation vectors to a system user, and allow the system user to select one or more electrostimulation vectors and program the electrostimulator circuit to deliver therapeutic electrostimulation to at least one site of the heart using the selected electrostimulation vectors.

Example 1 can include a system that comprises programmable electrostimulator circuit that can deliver electrostimulation to at least one site of the heart using a specified electrostimulation vector. The electrostimulator circuit can be a battery-powered implantable or ambulatory pulse generator that can deliver therapeutic stimulation to a heart. The system can include a physiologic sensor circuit that can sense one or more physiologic signals. The system can include a processor circuit that can generate at least a cardiac stimulation efficacy indicator and a battery longevity indicator using the one or more physiologic signals. The cardiac stimulation efficacy indicator can include a numerical or categorical value indicating a therapeutic effect of the electrostimulation of the heart using the specified electrostimulation vector, and the battery longevity indicator can include a numerical or categorical value indicating a battery status when the programmable electrostimulator circuit operates according to the specified electrostimulation vector. The system can include an electrostimulation vector assessment circuit included in or communicatively coupled to the processor circuit. For a plurality of candidate electrostimulation vectors, the electrostimulation vector assessment circuit can receive respective cardiac stimulation efficacy indicators and respective battery longevity indicators, and produce a rankable set of at least some of the plurality of candidate electrostimulation vectors using the respective cardiac stimulation efficacy indicators and the respective battery longevity indicators.

Example 2 can include, or can optionally be combined with the subject matter of Example 1 to optionally include, the electrostimulation vector assessment circuit that can generate first ranked vectors by ranking the at least some of the plurality of candidate electrostimulation vectors according to a first specified order of first indicators, and generate second ranked vectors by ranking at least a portion of the first ranked vectors according to a second specified order of second indicators. The portion of the first ranked vectors has corresponding first indicators that meet a specified condition. The first indicators are one, and the second indicators are the other, of the respective cardiac stimulation efficacy indicators or the respective battery longevity indicators.

Example 3 can include, or can optionally be combined with the subject matter of Example 2 to optionally include, the electrostimulation vector assessment circuit that can generate the first ranked vectors according to a descending order of the respective cardiac stimulation efficacy indicators, and generate the second ranked vectors according to a descending order of the respective battery longevity indicators.

Example 4 can include, or can optionally be combined with the subject matter of one or any combination of Examples 1 through 3 to include, the processor circuit that can further generate a complication indicator indicating non-cardiac activation produced by the electrostimulation to the heart. For the plurality of candidate electrostimulation vectors, the electrostimulation vector assessment circuit can further receive respective complication indicators from the processor circuit, and rank at least some of the plurality of candidate electrostimulation vectors further using the respective complication indicators.

Example 5 can include, or can optionally be combined with the subject matter of Example 4 to optionally include, the complication indicators each of which can include information about presence or absence of phrenic nerve activation in response to the electrostimulation to the heart, or one or more parameters including a phrenic nerve stimulation threshold ($PNS_T$) indicative of minimum electrostimulation intensity sufficient to elicit phrenic nerve activation, or a safety margin indicative of a relationship between the $PNS_T$ and a cardiac capture threshold.

Example 6 can include, or can optionally be combined with the subject matter of Example 5 to optionally include, the electrostimulation vector assessment circuit that can generate first ranked vectors by ranking the at least some of the plurality of candidate electrostimulation vectors according to a first specified order of first indicators, and generate second ranked vectors by ranking at least a portion of the first ranked vectors according to a second specified order of second indicators, where the portion of the first ranked vectors have corresponding first indicators that meet a specified condition. The electrostimulation vector assessment circuit can generate third ranked vectors by ranking at least a portion of the second ranked vectors according to a third specified order of third indicators, where the portion of the second ranked vectors have corresponding second indicators that meet a specified condition. The first, second, and third indicators can be mutually different and selected from the cardiac stimulation efficacy indicators, the battery longevity indicators, and the complication indicators.

Example 7 can include, or can optionally be combined with the subject matter of one or any combination of Examples 1 through 6 to include, a user interface unit that can be configured to display the ranked electrostimulation vectors, the corresponding respective cardiac stimulation efficacy indicators, and the corresponding respective battery longevity indicators. The user interface can also receive a user input, including a selection of at least one electrostimulation vector from the ranked electrostimulation vectors and programming the programmable electrostimulator circuit to deliver electrostimulation to the heart using the selected at least one electrostimulation vector.

Example 8 can include, or can optionally be combined with the subject matter of one or any combination of Examples 1 through 7 to include, the electrostimulation vector assessment circuit that can automatically select at least one electrostimulation vector from the ranked electrostimulation vectors. The programmable electrostimulator circuit can deliver electrostimulation to the heart using the selected at least one electrostimulation vector.

Example 9 can include, or can optionally be combined with the subject matter of one or any combination of Examples 1 through 8 to include, one or more left ventricle (LV) electrodes removably and respectively positionable at an LV of the heart. The programmable electrostimulator circuit can be configured to be electrically coupled to the one or more LV electrodes, and deliver LV electrostimulation using a specified LV electrostimulation vector involving at least one of the LV electrodes.

Example 10 can include, or can optionally be combined with the subject matter of Example 9 to optionally include, two or more unipolar LV electrostimulation vectors and two or more bipolar LV electrostimulation vectors. The electrostimulation vector assessment circuit can rank the two or more unipolar LV electrostimulation vectors using first cardiac stimulation efficacy indicators and first battery longevity indicators in response to LV electrostimulation using the two or more unipolar LV electrostimulation vectors. The electrostimulation vector assessment circuit can select, automatically or based on a user input, one or more unipolar LV electrostimulation vectors from the ranked unipolar LV electrostimulation vectors, and identify, from the two or more bipolar LV electrostimulation vectors, the bipolar vectors each of which involves at least one electrode used by the selected unipolar LV electrostimulation vectors. The electrostimulation vector assessment circuit can then rank the identified bipolar LV electrostimulation vectors using second cardiac stimulation efficacy indicators and second battery longevity indicators in response to LV electrostimulation using the identified bipolar LV electrostimulation vectors.

Example 11 can include, or can optionally be combined with the subject matter of Example 9 to optionally include, the electrostimulation vector assessment circuit that can select from the ranked LV electrostimulation vectors, automatically or based on a user input, at least first and second LV electrostimulation vectors. The programmable electrostimulator circuit can be configured to, during the same cardiac cycle, deliver a first LV electrostimulation using the first selected LV electrostimulation vector and deliver a second LV electrostimulation using the second selected LV electrostimulation vector.

Example 12 can include, or can optionally be combined with the subject matter of one or any combination of Examples 1 through 11 to include, the physiologic sensor circuit that can sense at least a cardiac electrical signal and a cardiac mechanical signal in response to the electrostimulation of the one or more sites of the heart according a specified electrostimulation vector. The processor circuit can generate one or more electrical signal metrics and one or more mechanical signal metrics using the cardiac electrical signal and the cardiac mechanical signal, and generate the cardiac stimulation efficacy indicator using the one or more electrical signal metrics and the one or more mechanical signal metrics.

Example 13 can include, or can optionally be combined with the subject matter of Example 12 to optionally include, the processor circuit that can generate the cardiac stimulation efficacy indicator including a composite score using a linear or nonlinear combination of at least some of the electrical signal metrics and the mechanical signal metrics.

Example 14 can include, or can optionally be combined with the subject matter of one or any combination of Examples 1 through 13 to include, the processor circuit that can be generate the battery longevity indicator using one or more of cardiac capture threshold, electrostimulation intensity, electrostimulation waveform, lead impedance, or number of electrodes involved in the specified electrostimulation vector.

Example 15 can include, or can optionally be combined with the subject matter of one or any combination of Examples 1 through 14 to include, one or more of a timer/clock circuit that can provide an indication of time of a day, a physical activity detector that can detect physical activity of the patient or an indication of metabolic demand of the patient, or a patient wellness detector that an produce an indication of a worsening or improvement of a disease state. The electrostimulation vector assessment circuit can rank at least some of the plurality of candidate electrostimulation vectors further using one or more of the detected time of a day, the patient metabolic demand, the patient activity level, or the indication of worsening or improvement of the disease state.

Example 16 can include a method for evaluating a plurality of candidate electrostimulation vectors for use in therapeutic stimulation of a heart. The method can comprise steps of delivering respective electrostimulation to at least one site of the heart using the plurality of candidate electrostimulation vectors, sensing respective one or more physiologic signals, and generating respective cardiac stimulation efficacy indicators and respective battery longevity indicators using the sensed respective one or more physiologic signals. The respective cardiac stimulation efficacy indicators each can include a numerical or categorical value indicating a therapeutic effect of the respective electrostimulation of the heart. The respective battery longevity indicators each can include a numerical or categorical value indicating a battery status when the programmable electrostimulator circuit respectively operates according to one of the plurality of electrostimulation vectors. The method can include ranking at least some of the plurality of candidate electrostimulation vectors using the respective cardiac stimulation efficacy indicators and the respective battery longevity indicators.

Example 17 can include, or can optionally be combined with the subject matter of Example 16 to optionally include, the method of ranking at least some of the plurality of candidate electrostimulation vectors which can include steps of generating first ranked vectors by ranking the at least some of the plurality of candidate electrostimulation vectors according to a first specified order of first indicators, and generating second ranked vectors by ranking at least a portion of the first ranked vectors according to a second specified order of second indicators. The portion of the first ranked vectors has corresponding first indicators that meet a specified condition. The first indicators can be one, and the second indicators can be the other, of the cardiac stimulation efficacy indicators or the battery longevity indicators.

Example 18 can include, or can optionally be combined with the subject matter of Example 17 to optionally include, the method of ranking at least some of the plurality of candidate electrostimulation vectors that can include generating the first ranked vectors according to a descending order of the cardiac stimulation efficacy indicators, and generating the second ranked vectors according to a descending order of the battery longevity indicators.

Example 19 can include, or can optionally be combined with the subject matter of Example 16 to optionally include, a method of generating respective complication indicators in response to the electrostimulation respectively delivered using the plurality of candidate electrostimulation vectors, and ranking at least some of the plurality of candidate electrostimulation vectors further using the respective complication indicators. Each complication indicator can be indicative of non-cardiac activation produced by the electrostimulation, and include one or more of presence or absence of phrenic nerve activation, a phrenic nerve stimulation threshold ($PNS_T$) indicative of minimum electrostimulation intensity sufficient to elicit phrenic nerve activation, or a safety margin indicative of a relationship between the $PNS_T$ and a cardiac capture threshold.

Example 20 can include, or can optionally be combined with the subject matter of Example 19 to optionally include, the method of ranking the candidate electrostimulation vectors which can include generating first ranked vectors by ranking the at least some of the plurality of candidate electrostimulation vectors according to a first specified order of first indicators, generating second ranked vectors by ranking at least a portion of the first ranked vectors according to a second specified order of second indicators, where the portion of the first ranked vectors have corresponding first indicators that meet a specified condition. The method can include generating third ranked vectors by ranking at least a portion of the second ranked vectors according to a third specified order of third indicators, where the portion of the second ranked vectors have corresponding second indicators that meet a specified condition. The first, second, and third indicators can be mutually different and selected from the cardiac stimulation efficacy indicators, the battery longevity indicators, and the complication indicators.

Example 21 can include, or can optionally be combined with the subject matter of Example 16 to optionally include, a method of displaying in a user interface unit the ranked electrostimulation vectors, the respective cardiac stimulation efficacy indicators, and the battery longevity indicators, and selecting at least one electrostimulation vector from the ranked electrostimulation vectors automatically or based on a user input. Example 21 can also include an operation of delivering electrostimulation to the heart using the selected at least one electrostimulation vector.

Example 22 can include, or can optionally be combined with the subject matter of Example 16 to optionally include, a method of delivering left ventricular (LV) pacing pulses to one or more LV sites using a plurality of candidate LV electrostimulation vectors including two or more unipolar LV electrostimulation vectors and two or more bipolar LV electrostimulation vectors. The method of ranking the plurality of candidate electrostimulation vectors can include ranking the two or more unipolar LV electrostimulation vectors using first cardiac stimulation efficacy indicators and first battery longevity indicators in response to LV electrostimulation using the two or more unipolar LV electrostimulation vectors, selecting, automatically or based on a user input, one or more unipolar LV electrostimulation vectors from the ranked unipolar LV electrostimulation vectors, and identifying, from the two or more bipolar LV electrostimulation vectors, bipolar LV electrostimulation vectors each involving at least one electrode used by the selected unipolar LV electrostimulation vectors. Example 22 can also include ranking the identified bipolar LV electrostimulation vectors using second cardiac stimulation efficacy indicators and second battery longevity indicators in response to LV electrostimulation using the identified bipolar LV electrostimulation vectors.

Example 23 can include, or can optionally be combined with the subject matter of Example 16, to optionally include the method of generating the respective cardiac stimulation efficacy indicators, which can include generating one or more electrical signal metrics and one or more mechanical signal metrics, and generating the cardiac stimulation efficacy indicator using a linear or nonlinear combination of at least some of the electrical signal metrics and the mechanical signal metrics. Example 23 can also include generating the respective battery longevity indicators using one or more of cardiac capture threshold, electrostimulation intensity, electrostimulation waveform, lead impedance, or number of electrodes involved in the specified electrostimulation vector.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for evaluating a plurality of candidate electrostimulation vectors for use in therapeutic stimulation of a heart. Electrostimulation can be delivered using a programmable electrostimulator circuit to one or more sites of a heart according to one of multiple candidate electrostimulation vectors. The resulting physiologic responses to electrostimulation can be analyzed to produce therapy efficacy indicators and battery longevity indicators. The candidate electrostimulation vectors can then be ranked according to specified orders of the therapy efficacy indicators and the battery longevity indicators. Ranked order of the candidate electrostimulation vectors can be displayed, and a system user can program the electrostimulator circuit to deliver therapeutic electrostimulation to at least one site of the heart using one or more vectors selected from the ranked electrostimulation vectors.

Figure 1:
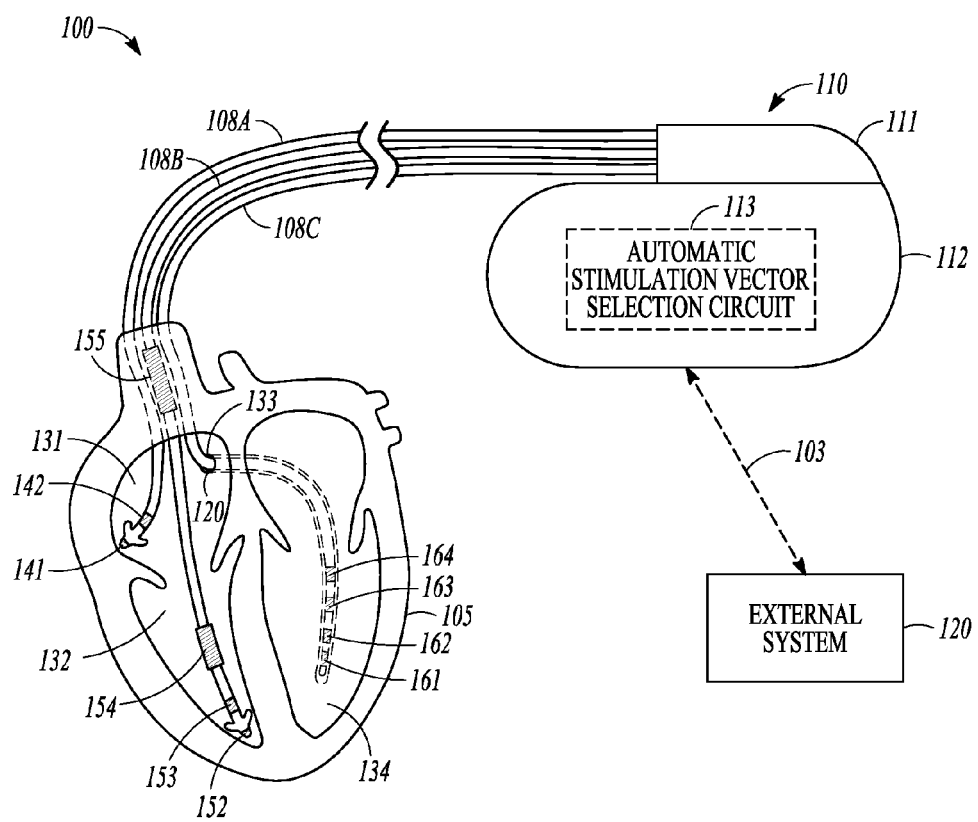
FIG. 1 illustrates generally an example of a Cardiac Rhythm Management (CRM) system and portions of an environment in which the CRM system can operate.

FIG. 1 illustrates generally an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed IMD can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing the LV electrogram and optionally allow delivery of one or more resynchronization pacing pulses from the LV. Additional electrodes can be included in or along the lead 108C. In an example, as illustrated in FIG. 1, a third electrode 163 and a fourth electrode 164 can be included in the lead 108. In some examples (not shown in FIG. 1), at least one of the leads 108A-C, or an additional lead other than the leads 108A-C, can be implanted under the skin surface without being within at least one heart chamber, or at or close to heart tissue.

The IMD 110 can include an electronic circuit that can sense a physiological signal. The physiological signal can include an electrogram or a signal representing mechanical function of the heart 105. The hermetically sealed IMB can 112 may function as an electrode such as for sensing or pulse delivery. For example, an electrode from one or more of the leads 108A-C may be used together with the IMD can 112 such as for unipolar sensing of an electrogram or for delivering one or more pacing pulses. A defibrillation electrode from the lead 108B may be used together with the IMB can 112 such as for delivering one or more cardioversion/defibrillation pulses. In an example, the IMD 110 can sense impedance such as between electrodes located on one or more of the leads 108A-C or the IMD can 112. The IMB 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include an automatic stimulation vector selection circuit 113. The automatic stimulation vector selection circuit 113 can be configured to detect physiologic responses to electrostimulation at one or more sites in at least one chamber of the heart 105, such as electrostimulation of the left ventricle (LV) 134 using one or more of the electrodes 161-164 on the lead 108C (which are hereinafter referred to as LV electrodes "LV1", "LV2", "LV3" and "LV4" electrodes). The automatic stimulation vector selection circuit 113 can determine therapeutic efficacy, such as patient hemodynamic outcome, of the electrostimulation based on an analysis of the detected physiologic responses. The automatic stimulation vector selection circuit 113 can additionally determine a battery status such as battery longevity of the IMD 110 when the IMD 110 operates according to the specified electrostimulation vector. For a plurality of candidate electrostimulation vectors, the automatic stimulation vector selection circuit 113 can generate respectively cardiac stimulation efficacy indicators and battery longevity indicators, and rank the candidate electrostimulation vectors using the cardiac stimulation efficacy indicators and the battery longevity indicators. The IMD 110 can be programmed to deliver electrostimulation to the heart, such as one or more sites of the LV 134, using at least one stimulation vector selected from the ranked candidate electrostimulation vectors. Examples of the automatic stimulation vector selection circuit 113 are described below, such as with reference to FIGS. 2-5.

The external system 120 can allow for programming of the IMB 110 and can receive information about one or more signals acquired by IMB 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMB operational status stored in the IMD 110, one or more programming instructions to the IMB 110 such as to configure the IMB 110 to perform one or more actions that can include physiological data acquisition such as using programmably specifiable sensing electrodes and configuration, device self-diagnostic test, or delivery of one or more therapies.

The automatic stimulation vector selection circuit 113 can be implemented at the external system 120 such as using data extracted from the IMB 110 or data stored in a memory within the external system 120. Portions of the automatic stimulation vector selection circuit 113 may be distributed between the IMB 110 and the external system 120.

Portions of the IMD 110 or the external system 120 can be implemented using hardware, software, or any combination of hardware and software. Portions of the IMB 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
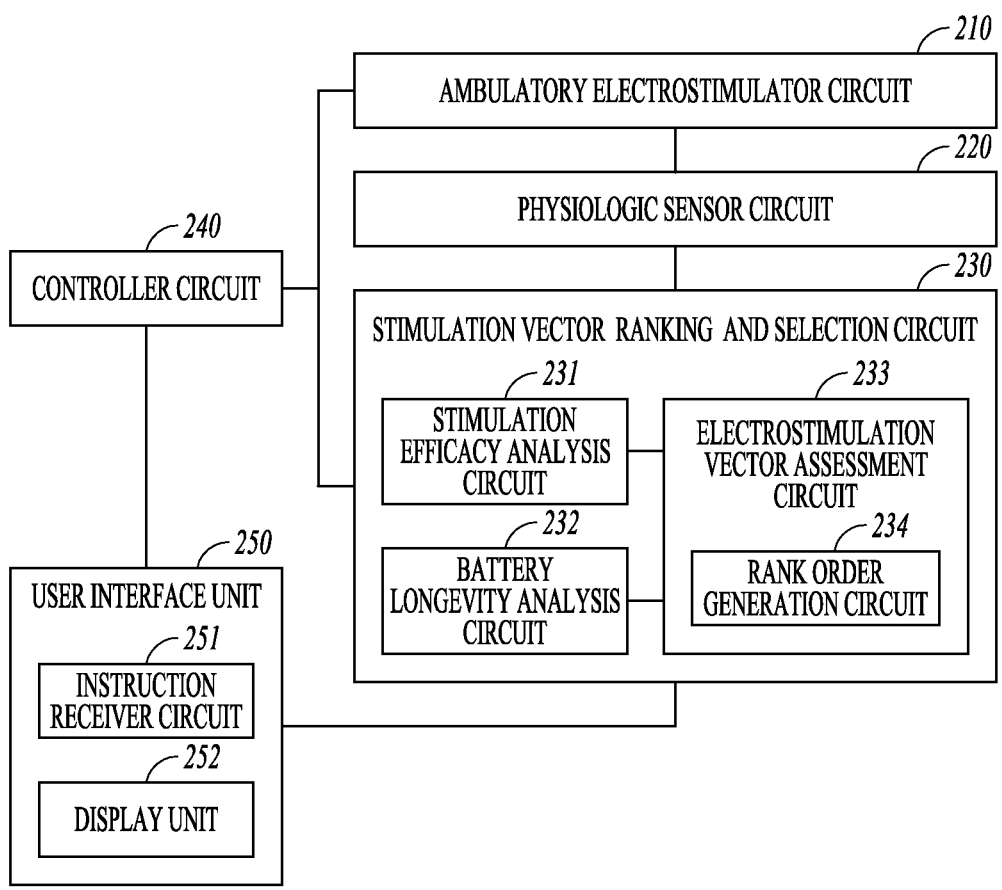
FIG. 2 illustrates generally an example of an automatic stimulation vector selection circuit.

FIG. 2 illustrates generally an example of an automatic stimulation vector selection circuit 200, which can be an embodiment of the automatic stimulation vector selection circuit 113. The automatic stimulation vector selection circuit 200 can include one or more of a programmable electrostimulator circuit 210, a physiologic sensor circuit 220, a stimulation vector ranking and selection circuit 230, a controller circuit 240, and a user interface unit 250.

The programmable electrostimulator circuit 210 can be a battery-powered implantable, wearable, or ambulatory pulse generator such as the IMD 100, or an external electrostimulation device. The programmable electrostimulator circuit 210 can be electrically coupled to a pacing delivery system that delivers pacing pulses to one or more sites of at least one chamber of the heart. The pacing delivery system can include one or more implantable leads (such as the leads 108A-C), stimulation catheters, or non-tethered pacing units, each including one or more stimulation electrodes. The parameters of the pacing pulses can be programmable, including pulse amplitude, pulse width, duty cycle, duration, or frequency, among others.

The programmable electrostimulator circuit 210 can deliver the electrostimulation using an electrostimulation vector that involves an anode electrode and a cathode electrode. In an example, the programmable electrostimulator circuit 210 can generate and deliver LV electrostimulation using one of a plurality of LV electrostimulation vectors. Each LV electrostimulation vector includes at least one of the anode or the cathode removably and respectively positionable at the LV. In an example, the LV electrostimulation vectors can include at least one unipolar LV electrostimulation vector involving an LV electrode and a reference electrode such as the IMD can 112. In another example, the LV electrostimulation vectors can include at least one bipolar LV electrostimulation vector involving two LV electrodes, an LV electrode and a RV electrode (such as one of the electrodes 152-155 on the RV lead 108B), or an LV electrode and a RA electrode (such as or the RA electrodes 141 and 142 on the RA lead 108A). In an example, the LV electrostimulation vectors can include a tripolar pacing between one or more LV electrodes and a RV or RA electrode.

The programmable electrostimulator circuit 210 can deliver the electrostimulation to two or more sites in the heart using respective electrostimulation vectors. The two or more sites can include anatomical regions inside, or on an epicardial surface of, a right atrium (RA), a right ventricle (RV), a left atrium (LA), a left ventricle (LV), or tissues surrounding any of the chambers. In an example, the programmable electrostimulator circuit 210 can deliver electrostimulation to two or more sites at the same chamber, such as two or more sites in LV, which is hereinafter referred to as "multi-site LV electrostimulation." The programmable electrostimulator circuit 210 can deliver multi-site LV electrostimulation using respective two or more LV electrostimulation vectors within a cardiac cycle, such as simultaneous stimulation or asynchronous stimulation separated by a specified temporal offset less than a sensed or paced time interval value of the cardiac cycle.

The physiologic sensor circuit 220 can sense a physiologic signal under a specified condition, such as when the heart is stimulated in accordance with a specified stimulation configuration. The physiologic sensor circuit 220 can additionally or alternatively sense an intrinsic physiologic activity without electrostimulation. The physiologic signal can be sensed using one or more ambulatory physiologic sensors or electrodes deployed at or near the heart. The sensing circuit can further process the sensed physiologic signals including amplification, digitization, filtering, or other signal conditioning processes.

The sensed physiologic signal can include cardiac electrical signals, such as electrocardiograms (ECGs) sensed by using electrodes non-invasively attached to the body surface, subcutaneous ECGs sensed by using subcutaneously placed electrodes, or intracardiac electrograms (EGMs) sensed by using electrodes on one or more of the leads 108A-C or the IMD can 112. In an example, the physiologic sensor circuit 220 can sense two or more intracardiac EGMs via respective sensing vectors, such as two or more LV EGMs using respective sensing vectors each including at least one of LV electrodes 161-164. LV EGMs can be sensed using a unipolar or a bipolar LV sensing vector. A unipolar LV sensing vector can involve one LV electrode and the IMD can 112. A bipolar LV sensing vector can involve any two of the LV electrodes 161-164 (which can be referred to as "true bipolar" pacing vector).

The sensed physiologic signal can additionally or alternatively include cardiac mechanical signals indicative of contractions of an atrium or a ventricle in response to electrostimulation of the heart. In an example, the cardiac mechanical activities can include a heart sound (HS) signal. The HS signal can be sensed using an ambulatory accelerometer, a microphone, or other implantable sensors associated with an implantable lead or a device can. In an example, the cardiac mechanical activities can include an impedance signal sensed using an impedance sensor configured to sense cardiac or thoracic impedance change as a result of cardiac contractions. In an example, the cardiac mechanical signals can include pressure signals indicative of pressures including one or more of arterial pressure, pulmonary artery pressure, left atrial pressure, RV pressure, LV coronary pressure. In another example, the cardiac mechanical signals can include signals indicative of volume of a chamber of the heart, which can be measured using cardiac impedance sensors. In some examples, other physiologic sensors can be used, including a temperature sensor configured to sense blood temperature or core body temperature, an optical sensor such as pulse oximeters configured for sensing blood oxygen saturation, or a chemical sensor configured for sensing central venous pH value, among others.

The stimulation vector ranking and selection circuit 230 can be configured to evaluate a plurality of candidate electrostimulation vectors for use in therapeutic stimulation of a heart. The stimulation vector ranking and selection circuit 230 can be implemented as a part of a microprocessor circuit within the automatic stimulation vector selection circuit 200. The microprocessor circuit can be a dedicated processor such as a digital signal processor, application specific integrated circuit (ASIC), microprocessor, or other type of processor for processing information including physical activity information. Alternatively, the microprocessor circuit can be a general purpose processor that can receive and execute a set of instructions of performing the functions, methods, or techniques described herein.

The stimulation vector ranking and selection circuit 230 can include one or more of a stimulation efficacy analysis circuit 231, a battery longevity analysis circuit 232, and an electrostimulation vector assessment circuit 233. The stimulation efficacy analysis circuit 231 can be configured to generate a cardiac stimulation efficacy indicator using one or more physiologic signals obtained during electrostimulation of the heart using a specified electrostimulation vector. The cardiac stimulation efficacy indicator can be a numerical or categorical value indicating a therapeutic effect of an electrostimulation of the heart, such as hemodynamic response to a cardiac resynchronization therapy (CRT) or multi-site LV electrostimulation therapy.

The stimulation efficacy analysis circuit 231 can produce one or more signal metrics using cardiac electrical or cardiac mechanical signals. The cardiac electrical or mechanical signals can be provided by the physiologic sensor circuit 220. Alternatively, the stimulation efficacy analysis circuit 231 can receive the cardiac electrical or mechanical signals from a storage device such as an electronic medical record (EMR) system, such as in response to a command signal provided by a system user (e.g., a clinician). The signal metrics of the cardiac electrical or mechanical signal can include temporal, statistical, or morphological features of one or more of the cardiac electrical or mechanical signals.

The stimulation efficacy analysis circuit 231 can generate the cardiac stimulation efficacy indicator as a linear or a non-linear combination of two or more electrical or mechanical signal metrics. The cardiac stimulation efficacy indicator can have a numerical value or a categorical value. In an example, the cardiac stimulation efficacy indicator has a numerical value, where a larger value indicates a higher therapeutic efficacy. In another example, the cardiac stimulation efficacy indicator has a descriptive categorical value selected from one or more of "very low", "low", "medium", "high", "very high", each indicating the level of therapeutic efficacy of the corresponding electrostimulation vector. Examples of the signal metrics and computation of the cardiac stimulation efficacy indicator are discussed below, such as with reference to FIG. 3.

The battery longevity analysis circuit 232 can be configured to generate a battery longevity indicator indicating a battery status such as projected remaining lifetime of the battery. Battery longevity can be affected by a number of factors, including battery chemistry and battery voltage and impedance, configuration of electrostimulation vectors, polarity and number of electrodes that form a stimulation vector, lead impedance, capture threshold indicative of minimum amount of energy required to generating a propagating cardiac depolarization, mode or sequence of electrostimulation which determines the "ON" time for delivery of electrostimulation, stimulation parameters including pulse amplitude, pulse width, frequency, duty cycle, among others. In one example, the battery longevity can be estimated using a model of battery capacity and expected circuit performance, such as described by Russie, in U.S. Pat. No. 7,620,452, entitled "Systems and Methods for Managing the Longevity of an Implantable Medical Device Battery," which is herein incorporated by reference in its entirety. In another example, the longevity can be calculated based on sensed capacity as measured by a coulometer or a capacity-by-voltage device, such as described by Gandhi et al. in U.S. Pat. No. 8,055,343, entitled "Dynamic battery management in an implantable device," which is herein incorporated by reference in its entirety.

The battery longevity indicator can have a numerical value or a categorical value. In an example, the battery longevity indicator has a numerical value of the projected remaining lifetime (e.g., years) of the battery. In another example, the battery longevity indicator has a categorical value of a range of remaining lifetime, such as one or more of "<1 year", "1-3 years", "3-5 years", ">5 years". The battery longevity indicator can include a relative longevity such as with respect to reference longevity. In an example, the reference longevity can be corresponding to the lifetime of the battery at its full capacity (e.g., a new battery before discharge), and the battery longevity indicator can indicate a fraction or percentage of the referenced longevity (e.g., ⅓, 25%, or half of full capacity).

The electrostimulation vector assessment circuit 233 can be communicatively coupled to the stimulation efficacy analysis circuit 231 and the battery longevity analysis circuit 232, and receive the cardiac stimulation efficacy indicators corresponding to the respective plurality of candidate electrostimulation vectors, and the battery longevity indicators when the programmable electrostimulator circuit respectively operates according to the plurality of candidate electrostimulation vectors. The electrostimulation vector assessment circuit 233 can include a rank order generation circuit 234 that can produce a rankable set of at least some of the plurality of candidate electrostimulation vectors using the cardiac stimulation efficacy indicators and the battery longevity indicators.

In an example, the rank order generation circuit 234 can perform multi-level ranking on at least some of the candidate electrostimulation vectors, such as by generating first ranked vectors according to a first specified order of first indicators, and then generate second ranked vectors by ranking at least a portion of the first ranked vectors according to a second specified order of second indicators. The portion of the first ranked vectors has corresponding first indicators that meet a specified condition. The first indicators can be one, and the second indicators can be the other, of the cardiac stimulation efficacy indicators or the battery longevity indicators. In an example, the rank order generation circuit 234 can first rank the candidate electrostimulation vectors according to a descending order of the cardiac stimulation efficacy indicators, and then rank the ordered electrostimulation vectors according to a descending order of the battery longevity indicators. Table 1 illustrates an example of a ranked list of LV electrostimulation vectors for potential use in CRT pacing, such as presented in a display unit of a user interface. The vectors are ranked first according to a descending order of numerical scores of the therapy efficacy indicators. Then, at least a portion of the first ranked vectors that have identical therapy efficacy indicators, or that have therapy efficacy indicators falling with a specified range, can be identified. Such identified portion of the vectors can be ranked according to a descending order of number of years remaining in battery life. For example, LV electrostimulation vectors having the same therapy efficacy indicator (e.g., vectors LV1-Can and LV1-LV4) are further ranked such that the vector having a longer battery life (e.g., LV1-Can) has a higher priority on the list than the vector having shorter battery life (e.g., LV1-LV4).

TABLE 1

| LV electrostimulation vectors | Therapy efficacy Indicator | Battery Longevity Indicator |
| --- | --- | --- |
| LV1-Can | 9 | 8 years |
| LV1-LV4 | 9 | 7.5 years |
| LV2-Can | 8 | 8 years |
| LV1-LV2 | 8 | 4 years |
| LV4-Can | 6 | 5 years |

In an example, in addition to or in lieu of the cardiac stimulation efficacy indicator computed using combined electrical and mechanical signal metrics, the stimulation efficacy analysis circuit 231 can generate a first stimulation efficacy indicator using only the electrical signal metrics, and a second stimulation efficacy indicator using only the mechanical signal metrics. The first and second stimulation efficacy indicators can be separately and independently used in multi-level ranking of the candidate electrostimulation vectors, along with the battery longevity indicators. In an example, the rank order generation circuit 234 can perform multi-level ranking on at least some of the candidate electrostimulation vectors using the battery longevity indicators and only one of the first or the second stimulation efficacy indicators. In another example, the rank order generation circuit 234 can perform multi-level ranking using the battery longevity indicators, and both the first and second stimulation efficacy indicators. As an example, the multi-level ranking can include generating first ranked vectors according to a descending order of the first stimulation efficacy indicators, then generating second ranked vectors by ranking at least a portion of the first ranked vectors according to a descending order of the second stimulation efficacy indicators, and then generating third ranked vectors by ranking at least a portion of the second ranked vectors according to a descending order of the battery longevity indicators.

The controller circuit 240 can control the operations of the programmable electrostimulator circuit 210, the physiologic sensor circuit 220, the stimulation vector ranking and selection circuit 230, and the data flow and instructions between these components and respective subcomponents. For a plurality of candidate electrostimulation vectors, either stored in a memory of the automatic stimulation vector selection circuit 200 or received from a system user such as via the user interface unit 250, the controller circuit 240 can configure the programmable electrostimulator circuit to deliver respective electrostimulation to the heart using the electrostimulation vectors, and configure the physiologic sensor circuit 220 to sense one or more electrical or mechanical signals during the delivery of the respective electrostimulation. The controller circuit 240 can configure the stimulation efficacy analysis circuit 231 and the battery longevity analysis circuit 232 to generate respectively the cardiac electrostimulation efficacy indicators and the battery longevity indicators corresponding to the candidate electrostimulation vectors. The controller circuit 240 can configure the electrostimulation vector assessment circuit 233 to rank the candidate electrostimulation vectors in an order such as specified by a system user via the user interface unit 250.

The user interface unit 250 can include an instruction receiver circuit 251 and a display unit 252. In an example, at least a portion of the user interface unit 250, such as the display unit, can be implemented in the external system 120.

The instruction receiver circuit 251 can include an input device that enables a system user to program the parameters used for electrostimulation or for sensing the physiologic signals. Examples of the input device can include a keyboard, on-screen keyboard, mouse, trackball, touchpad, touch-screen, or other pointing or navigating devices. The input device can also enable the system user to input, or choose from a set of predetermined factors (e.g., the electrostimulation efficacy indicators and the battery longevity indicators) and ranking methods (e.g., ascending or descending order for each factor, or a sequence used for multi-level ranking) for prioritizing the candidate electrostimulation vectors.

The input device can enable the system user to select or deselect at least one electrostimulation vector from the ranked electrostimulation vectors, and program the programmable electrostimulator circuit 210 to deliver electrostimulation to the heart using the selected at least one electrostimulation vector. In an example, two or more electrostimulation vectors can be selected from the ranked candidate electrostimulation vectors using the input device, and the controller circuit 240 can configure the programmable electrostimulator circuit 210 to deliver multi-site stimulation using the selected two or more electrostimulation vectors during the same cardiac cycle, simultaneously or separated by a specified temporal offset less than a sensed or paced interval value of a cardiac cycle. Electrostimulation using each of the selected vectors can be individually programmed such as by adjusting one or more stimulation parameters including amplitude, pulse width, duty cycle, duration, or frequency.

The display unit 252 can be configured to display information including device programming, device status such as lead impedance and integrity, battery status such as remaining lifetime of the battery, or cardiac capture threshold, among others. The information displayed at the display unit 252 can be presented in a human-perceptible medium format. In an example, the display unit 252 can be configured to display the ranked electrostimulation vectors, the respective cardiac stimulation efficacy indicators, and the battery longevity indicators in a table, a chart, a diagram, or other textual, tabular, or graphical presentation formats. This allows the system user to quickly and more effectively interpret relative performances of the candidate electrostimulation vectors and select one or more vectors. In an example, the display unit 252 can display, such as upon receiving user's selection via the user input device, one or more electrical or mechanical signal metrics used for computing the cardiac stimulation efficacy indicators, or one or more signal metrics used for generating the battery longevity indicators such as cardiac capture threshold, lead impedance, mode or sequence of electrostimulation, among others.

The automatic stimulation vector selection circuit 200 can optionally include a vector selection circuit configured to automatically select at least one electrostimulation vector from the ranked electrostimulation vectors. The programmable electrostimulator circuit 210 can automatically deliver electrostimulation to the heart using the selected at least one electrostimulation vector. In an example, the vector selection circuit can automatically select two or more LV electrostimulation vectors from the ranked electrostimulation candidate vectors, and the programmable electrostimulator circuit 210 can deliver multi-site LV electrostimulation using the two or more LV electrostimulation vectors within a cardiac cycle, such as simultaneous stimulation or asynchronous stimulation separated by a specified temporal offset less than a sensed or paced time interval value of the cardiac cycle.

Figure 3:
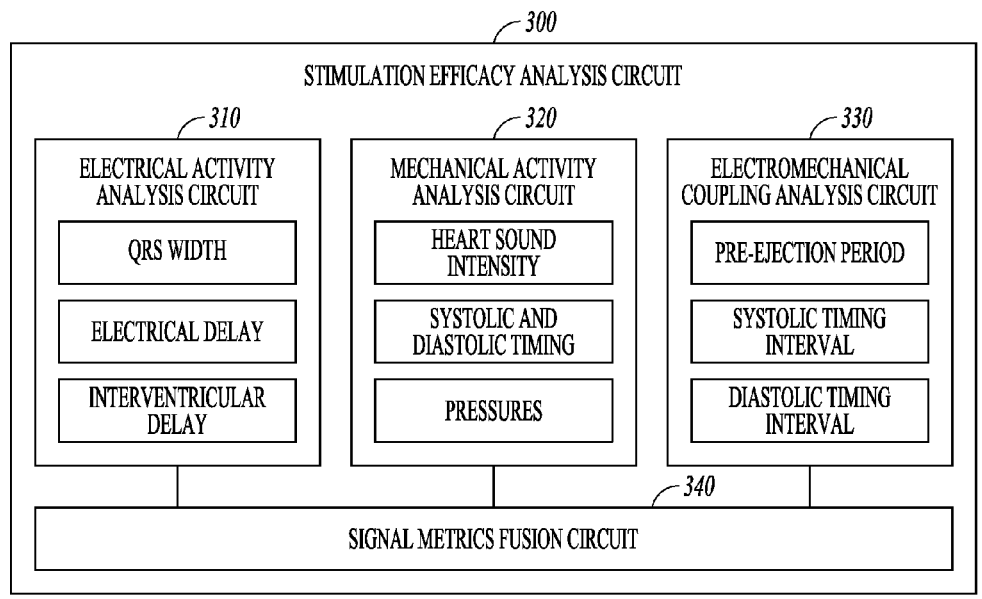
FIG. 3 illustrates generally an example of a stimulation efficacy analysis circuit.

FIG. 3 illustrates generally an example of a stimulation efficacy analysis circuit 300, which can be an embodiment of the stimulation efficacy analysis circuit 231. The stimulation efficacy analysis circuit 300 can produce a cardiac stimulation efficacy indicator used for generating a ranked order of a plurality of LV electrostimulation vectors for use in CRT therapy or multi-site LV electrostimulation therapy in HF patients. The stimulation efficacy analysis circuit 300 can include one or more of an electrical activity analysis circuit 310, a mechanical activity analysis circuit 320, an electromechanical coupling analysis circuit 330, and a signal metrics fusion circuit 340. Each of the circuits 310, 320 and 330 can generate respective categories of signal metrics that are indicative of therapeutic efficacy of the electrostimulation to the heart.

The electrical activity analysis circuit 310 can generate a group of electrical signal metrics using one or more cardiac electrical signals such as produced by the physiologic sensor circuit 220. Examples of the electrical signal metrics can include: intensities (such as amplitudes) and timing of P wave, Q wave, R wave, QRS complex, or T wave detected from a surface ECG or a subcutaneous ECG; timing of sensed activation of at least a portion of a chamber of the heart such as RA, RV, and LV, obtained from the intracardiac EGMs; QRS width; electrical delay of a chamber of the heart such as LV electrical delay; interventricular conduction delay measured as the delay between LV activation to RV activation (LV-RV) delay; intraventricular delay, among others. The electrical signal metrics can be predictive of patient hemodynamic response to the therapeutic cardiac electrostimulation. For example, the electrical delay can include a Q-LV interval measured from Q wave to left ventricle activation, measured from the onset of the intrinsic QRS (such as from the surface ECG) to local intrinsic activation at the LV stimulation site (such as detected as the first dominant peak on the LV electrogram). The Q-LV interval can be correlated with maximum rate of increase in LV pressure (LV dP/dt max, a clinical index to characterize the contractile ability of the heart), thus indicative of LV contractility. Q-LV interval therefore can be used to assess efficacy of the LV electrostimulation therapy delivered using a specified pacing vector.

The mechanical activity analysis circuit 320 can generate a group of mechanical signal metrics using one or more cardiac mechanical signals such as produced by the physiologic sensor circuit 220. Examples of mechanical signal metrics can include: intensity of a component of the sensed HS signal including one or more of S1, S2, S3, or S4 heart sounds; mechanical delay such as time intervals indicative of systole or diastole; pressures inside a heart chamber; end-systolic volume; or end-diastolic volume; among others. The intensity measure can include signal amplitude, slope or rate of change of signal amplitude, amplitude of a transformed physiologic signal such as integrated signal, or a frequency-domain measurement such as power spectral density. The mechanical signal metrics can be predictive of patient hemodynamic response to the therapeutic cardiac electrostimulation. In an example, intensity of S1 heart sounds (such as S1 amplitude) can be correlated with LV dP/dt max, thus indicative of the LV contractility. In another example, the mechanical delay can include left-ventricular ejection time (LVET), an interval from the opening to the closing of the aortic valve (mechanical systole). The LVET can be correlated with hemodynamic of the LV, and can be measured as an interval between S1 and S2 heart sound within the same cardiac cycle. S1 intensity and LVET therefore can both be used to assess efficacy of the LV electrostimulation therapy delivered using a specified pacing vector.

The electromechanical coupling analysis circuit 330 can use both a cardiac electrical signal and a cardiac mechanical signal to produce one or more electromechanical metrics indicative of electromechanical coupling of the heart. The electromechanical metrics can include cardiac timing intervals, such as a pre-ejection period (PEP), a systolic timing interval (STI), or a diastolic timing interval (DTI), among others. The PEP represents the total duration of the electrical and mechanical events prior to ejection, and can be measured as the time duration from the onset of the QRS to the S1 heart sound, that is, PEP≈Q-S1 interval. Alternatively, the PEP can be measured from the ventricular pacing (Vp) signal to the beginning of ventricular ejection such as represented by the onset of S1 heart sound, that is, PEP≈Vp-S1 interval. The STI represents the duration of total electromechanical systole, and contains two major components, namely the PEP and the LVET. The STI can be measured as an interval from the onset of the QRS complex on the ECG or the atrial activation event in an intracardiac EGM to the S2 heart sound, that is, STI≈Q-S2 interval. In the case when the ventricle is paced (Vp), the STI can be measured from the ventricular pacing (Vp) signal to the end of ventricular ejection such as represented by the onset of S2 heart sound, that is, STI≈Vp-S2 interval. The DTI represents the duration of total electro-mechanical diastole. The DTI spans from the closure of the aortic valve to the onset of the atrial depolarization in the next cardiac cycle. In an example, the DTI can be measured as the interval from the S2 heart sound to the onset of the QRS complex on the ECG or the atrial activation event in an intracardiac EGM of the next cardiac cycle, that is, DTI≈S2-Q interval.

In some examples, the signal metrics can include composite measures using two or more of the STI, the DTI, the PEP, the cardiac cycle (CL), or the LVET. Examples of the composite measures can include PEP/LVET ratio, STUDTI ratio, STU cycle length (CL) ratio, or DTUCL ratio, among others.

The signal metrics fusion circuit 340 can generate a composite score using at least some of the signal metrics produced by the signal metrics from the electrical activity analysis circuit 310, the mechanical activity analysis circuit 320, or the electromechanical coupling analysis circuit 330. The composite score can have a numerical or categorical value. In an example, each signal metric can be assigned a score indicative of stimulation efficacy. In another example, each category of signal metrics (e.g., each of the three categories of signal metrics respectively produced by circuits 310, 320 and 330) can be assigned a score indicative of stimulation efficacy. The signal metrics fusion circuit 340 can compute the composite score using a linear or non-linear fusion algorithm of the individual scores of the respective signal metrics, or the individual scores of the respective categories of signal metrics. Examples of the fusion algorithm can include decision trees, voting, weighted averages, neural networks, among others. The composite score can be indicative of the therapeutic efficacy of the cardiac stimulation. In various examples, the composite score can be presented as one of a risk level for a patient developing future worsening of HF, a hazard ratio relative to a reference population, average time to first medical intervention, or a degree of restoration or improvement of cardiac function, among others.

Figure 4:
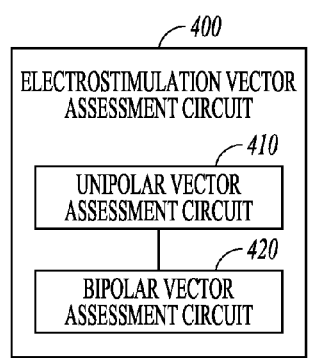
FIG. 4 illustrates generally an example of an electrostimulation vector assessment circuit.

FIG. 4 illustrates generally an example of an electrostimulation vector assessment circuit 400, which can be an embodiment of the electrostimulation vector assessment circuit 233. The electrostimulation vector assessment circuit 400 can be configured to select at least one unipolar electrostimulation vector and at least one bipolar electrostimulation vector using the selected at least one unipolar vector. The electrostimulation vector assessment circuit 400 can include a unipolar vector assessment circuit 410 and a bipolar vector assessment circuit 420.

The unipolar vector assessment circuit 410 can select at least one vector from a plurality of unipolar electrostimulation vectors, each of which can involve an electrode positioned at or near a target stimulation site of the heart (such as an electrode on one of the leads 108A-C), and a return electrode such as the IMD can 112. In an example of LV electrostimulation, a unipolar LV electrostimulation vector can involve a cathode being an LV electrode, such as one of the electrodes 161-164 along the LV lead 108C, and an anode being the IMD can 112. For the candidate unipolar LV electrostimulation vectors "LV1-Can", "LV2-Can", "LV3-Can", and "LV4-Can", the unipolar vector assessment circuit 410 can generate a ranked list of candidate unipolar LV electrostimulation vectors, such as by using the cardiac electrostimulation efficacy indicators such as provided by the stimulation efficacy analysis circuit 231 or the stimulation efficacy analysis circuit 300, and the battery longevity indicators such as provided by the battery longevity analysis circuit 232. The unipolar vector assessment circuit 410 can also select, automatically or based on a user input, at least one unipolar LV electrostimulation vector from the ranked unipolar LV electrostimulation vectors.

The bipolar vector assessment circuit 420 can be configured to rank a plurality of bipolar electrostimulation vectors. In an example of LV electrostimulation, a bipolar LV electrostimulation vector can involve a cathode and an anode both positioned at or near the LV, such as the electrodes 161-164 along the LV lead 108C. This configuration can be referred to as a "true bipolar" pacing vector. The bipolar LV electrostimulation vector can also be configured as between an LV electrode and another electrode positioned on a different chamber or on a different lead, such as one of electrodes 152-155 on the RV lead 108B, or electrodes 141 or 142 on the RA lead 108A. This configuration can be referred to as "extended bipolar" pacing vector to distinguish from the "true bipolar" pacing vector.

As illustrated in FIG. 4, the bipolar vector assessment circuit 420 can be coupled to the unipolar vector assessment circuit 410, and receive the ranking of the unipolar pacing vectors including information about the electrodes involved in the selected unipolar LV electrostimulation vectors. The bipolar vector assessment circuit 420 can identify, from the candidate bipolar LV electrostimulation vectors, one or more vectors each involving a cathode or an anode that is also used by the selected unipolar LV electrostimulation vector. The bipolar vector assessment circuit 420 can then rank the identified bipolar LV electrostimulation vectors using the cardiac electrostimulation efficacy indicators and the battery longevity indicators corresponding to each of the identified bipolar LV electrostimulation vectors. In an example, a bipolar LV electrostimulation vector with both the cathode and the anode involved in the selected unipolar LV electrostimulation vectors can be ranked at a higher priority than a bipolar LV electrostimulation vector that has only one electrode involved in the selected unipolar LV electrostimulation vectors. As an example, if the unipolar vector assessment circuit 410 selects unipolar LV electrostimulation vectors "LV1-Can" and "LV2-Can", the bipolar vector assessment circuit 420 can identify the bipolar LV electrostimulation vectors that involve at least one of the electrodes LV1 and LV2, such as bipolar pacing vectors LV1-LV2, LV1-LV3, LV1-RVring, or LV2-LV4. By contrast, bipolar LV electrostimulation vectors such as LV3-LV4, LV3-RVtip, or LV4-RVring will not be chosen for subsequent ranking of bipolar pacing vectors, as they does not involve at least one of the electrodes LV1 or LV2. Among the identified bipolar pacing vectors, the vector LV1-LV2 includes both the cathode and the anode that are involved in the selected unipolar LV electrostimulation vectors, it thus can be ranked at a higher priority than the rest of the bipolar pacing vectors. As another example, if the unipolar vector assessment circuit 410 selects only one unipolar LV electrostimulation vector "LV1-Can", then the bipolar vector assessment circuit 420 can identify and rank only those bipolar pacing vectors each involving at least the electrode LV1.

Figure 5:
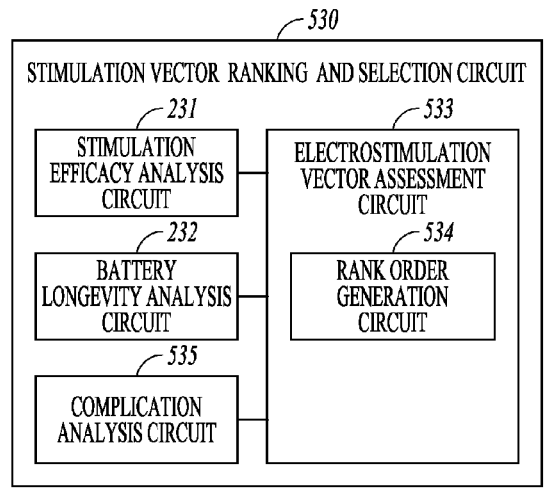
FIG. 5 illustrates generally an example of a stimulation vector ranking and selection circuit.

FIG. 5 illustrates generally an example of a stimulation vector ranking and selection circuit 530, which can be an embodiment of the stimulation vector ranking and selection circuit 230. The stimulation vector ranking and selection circuit 530 can include the stimulation efficacy analysis circuit 231 and the battery longevity analysis circuit 232, as included in the stimulation vector ranking and selection circuit 230. Additionally, the stimulation vector ranking and selection circuit 530 can include a complication analysis circuit 535, which can be configured to detect a complication indicator indicating non-cardiac activation produced by the electrostimulation to the heart using a specified electrostimulation vector. The complication indicator can include one or more indications of extra-cardiac stimulation or non-cardiac muscle stimulation, such as stimulation of skeletal muscle, diaphragm, phrenic nerve stimulation (PNS), unintended nerve stimulation, anodal cardiac stimulation, or any other parameters that do not support intended cardiac therapeutic effect. The unintended nerve or skeletal muscle stimulation can be caused by excessive energy delivered to the heart such as due to a high capture threshold, or close proximity between the cardiac stimulation electrode and the nerves or the skeletal muscle.

In an example, the complication analysis circuit 535 can be coupled to an accelerometer sensor configured to sense skeletal muscle activation in response to the cardiac electrostimulation delivered using a specified electrostimulation vector. In another example, the complication analysis circuit 535 can be coupled to a microphone sensor or an electromyogram (EMG) sensor to detect an activation of the laryngeal muscles, such as coughing response to undesirable activation of the laryngeal muscles or nerves caused by the electrostimulation delivered using a specified electrostimulation vector.

In an example, the complication analysis circuit 535 can detect the phrenic nerve activation such as by using an accelerometer or other sensors during delivery of cardiac electrostimulation. The presence or absence of phrenic nerve activation in response to the electrostimulation at a specified level can be detected by comparing the accelerometer signal intensity to a specified threshold value. Detection of the phrenic nerve activation can also include determining one or more parameters including a phrenic nerve stimulation threshold ($PNS_T$) representing minimum stimulation energy sufficient to elicit phrenic nerve activation, or a safety margin for phrenic nerve activation, which can be determined as a relationship between the $PNS_T$ and the cardiac capture threshold.

The complication analysis circuit 535 can determine the phrenic nerve activation parameters by delivering electrostimulation using a specified electrostimulation vector. The energy delivered can also be used to simultaneously search for a cardiac capture threshold, which represents minimum stimulation energy or voltage sufficient to elicit a propagating cardiac depolarization. If no phrenic nerve activation is sensed using the stimulation energy delivered, the energy level can be increased in subsequent trials of electrostimulation, until phrenic nerve activation is detected. The energy level at which phrenic nerve activation is detected can be the PNS threshold ($PNS_T$). Alternatively, the level of stimulation energy may be decreased or otherwise adjusted until phrenic nerve activation is not detected.

The electrostimulation vector assessment circuit 533 can receive respective complication indicators from the complication analysis circuit 535 in response to electrostimulation respectively delivered using a plurality of candidate electrostimulation vectors. The electrostimulation vector assessment circuit 533 can produce a rankable set of at least some of the plurality of candidate electrostimulation vectors using the complication indicators, as well as the stimulation efficacy indicators and the battery longevity indicators. The rank order generation circuit 534 can automatically, or upon receiving a user command, perform ranking of the candidate electrostimulation vectors. In an example, the rank order generation circuit 534 can perform a multi-level ranking of at least some of the candidate electrostimulation vectors, such as by generating first ranked vectors according to a first specified order of first indicators, generating second ranked vectors by ranking at least a portion of the first ranked vectors according to a second specified order of second indicators, where the portion of the first ranked vectors have corresponding first indicators that meet a specified condition, and generating third ranked vectors by ranking at least a portion of the second ranked vectors according to a third specified order of third indicators, where the portion of the second ranked vectors have corresponding second indicators that meet a specified condition. The first, second, and third indicators each can be selected from the cardiac stimulation efficacy indicators, the battery longevity indicators, and the complication indicators. In an example, the first, second, and third indicators can be, respectively, the cardiac stimulation efficacy indicators, complication indicators, and the battery longevity indicators.

Because phrenic nerve innervates the diaphragm, a stimulation of the phrenic nerve can cause a patient to experience a hiccup. The hiccup can be uncomfortable for the patient, interfere with normal breathing, and interfere with the intended therapeutic effect of the cardiac electrostimulation. As such, absence of phrenic nerve activation, a higher $PNS_T$, or a larger safety margin, is generally preferred over the presence of phrenic nerve activation, a lower $PNS_T$, or a smaller safety margin. In an example, an LV electrostimulation vector corresponding to a higher $PNS_T$ or a larger safety margin can be ranked at a higher priority in the ranked order of the candidate electrostimulation vectors. In an example, the rank order generation circuit 534 can first rank the candidate electrostimulation vectors according to a descending order of the cardiac stimulation efficacy indicators, rank the ordered electrostimulation vectors produced by the first ranking according to a descending order of the $PNS_T$ or the safety margin, and rank the ordered electrostimulation vectors produced by the second ranking according to a descending order of the battery longevity indicators. Table 2 illustrates an example of ranked list of LV electrostimulation vectors for CRT pacing or multi-site LV electrostimulation therapy, such as presented in a display unit of a user interface. The vectors are ranked using a multi-level method. For examples, the vectors can be first ranked according to the therapy efficacy indicators in a descending order. At least a portion of the first ranked vectors that have identical therapy efficacy indicators (or that have therapy efficacy indicators falling with a specified range) can then be identified, and the identified portion of the vectors can be ranked according to a descending order of the $PNS_T$. Then, at least a portion of the second ranked vectors that have identical $PNS_T$ values (or that have $PNS_T$ values that fall with a specified range) can be identified, and the identified portion of the vectors can be ranked according to the battery longevity.

TABLE 2

| LV electrostimulation vectors | Therapy efficacy Indicator | Phrenic Nerve Activation Threshold | Battery Longevity Indicator |
|---|---|---|---|
| LV1-Can | 9 | 8 volts | 8 years |
| LV1-LV4 | 9 | 5 volts | 7.5 years |
| LV2-Can | 8 | 7 volts | 8 years |
| LV1-LV2 | 8 | 4 volts | 4 years |
| LV4-Can | 6 | 9 volts | 5 years |

Alternatively or additionally, the stimulation vector ranking and selection circuit 530 can include one or more of a timer/clock circuit configured to provide an indication of time of a day, a physical activity detector circuit configured to detect physical activity level of the patient including a rest state or a physically active state or an indication of metabolic demand of the patient, or a patient wellness detector for providing indication of a worsening or improvement of a disease state such as myocardial infarction, cardiac arrhythmias, or heart failure, among others. The electrostimulation vector assessment circuit 533 can rank at least some of the plurality of candidate electrostimulation vectors using one or more of the information about time of a day, the patient activity level, the indication of metabolic demand, or the progression of the disease state, such as in addition to the therapy efficacy indicators, the battery longevity indicators, or the complication indicators.

Figure 6:
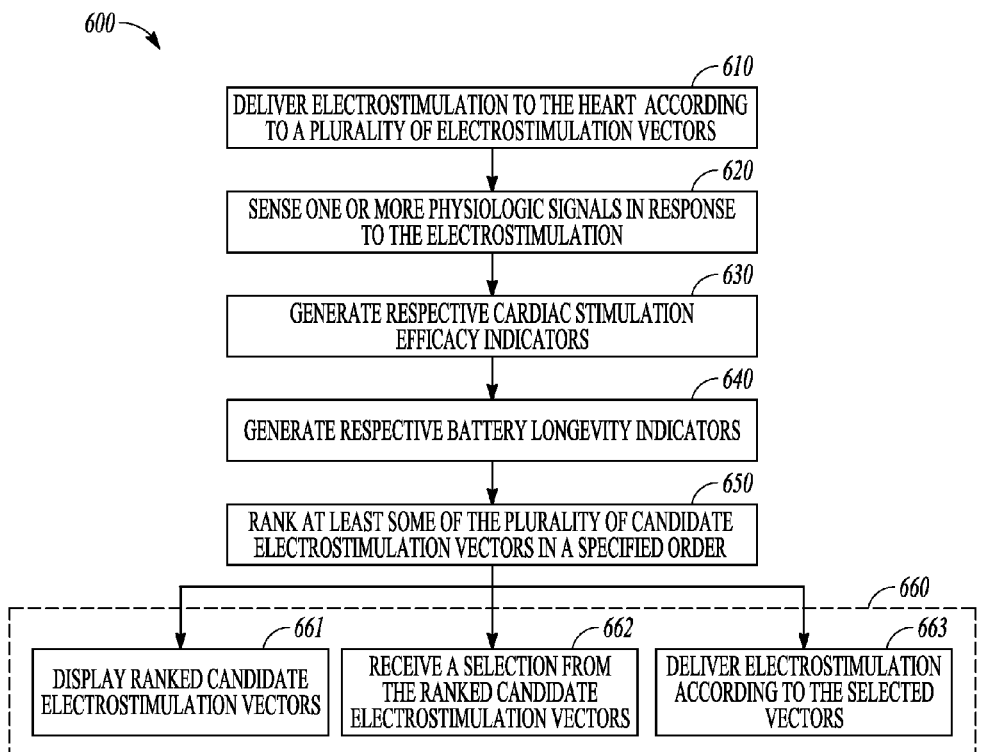
FIG. 6 illustrates generally an example of a method for evaluating a plurality of candidate electrostimulation vectors such as for use in therapeutic cardiac stimulation.

FIG. 6 illustrates generally an example of a method 600 for evaluating a plurality of candidate electrostimulation vectors such as for use in therapeutic cardiac stimulation. The method 600 can be implemented and executable in an implantable, wearable, or other ambulatory medical device, a programmer for programming an implantable device, or a remote patient management system. In an example, the method 600 can be performed by the automatic stimulation vector selection circuit 200, or any modification thereof.

The method 600 can begin at step 610, where electrostimulation can be delivered to one or more sites of at least one chamber of the heart using a plurality of candidate electrostimulation vectors. Each candidate electrostimulation vector comprises an anode and a cathode, and the electrostimulation can be delivered between the anode and the cathode. The electrostimulation can comprise one or more pulses generated by an implantable, wearable, or ambulatory pulse generator, or an external electrostimulation device. In an example, the electrostimulation can be delivered to one or more sites at the left ventricle (LV) of the heart, using each of a plurality of LV electrostimulation vectors. At least one of the anode or the cathode of each LV electrostimulation vector can be an LV electrode positioned at a site of LV of the heart. In an example, the LV electrostimulation vectors can include at least one unipolar LV electrostimulation vector involving an LV electrode and a reference electrode such as the IMD can 112. In another example, the LV electrostimulation vectors can include at least a bipolar LV electrostimulation vector involving two LV electrodes, an LV electrode and a RV electrode, or an LV electrode and a RA electrode.

At 620, one or more physiologic signals can be sensed in response to the delivery of electrostimulation using one of the electrostimulation vectors. The sensed physiologic signals can include one or more of cardiac electrical signals, cardiac mechanical signals, temperature signals, chemical sensor signals, among others. The cardiac electrical signals can include surface electrocardiograms (ECGs), subcutaneous ECGs, or intracardiac electrograms (EGMs) sensed by using implantable electrodes, such as one or more of the leads 108A-C or the IMD can 112. The cardiac mechanical signals can include heart sounds (HS) signals such as produced by an ambulatory accelerometer or a microphone, thoracic or cardiac impedance signals, pressure signals such as arterial pressure, pulmonary artery pressure, left atrial pressure, RV pressure, LV coronary pressure, volume signals (such as based on one more intracardiac impedance) indicative of volume of a chamber of the heart, or any other sensor signals indicative of contractions of an atrium or a ventricle in response to the electrostimulation of the heart.

At 630, a cardiac stimulation efficacy indicator can be generated using one or more physiologic signals obtained during electrostimulation of the heart using a specified electrostimulation vector. The cardiac stimulation efficacy indicator can be a numerical or categorical value indicating a therapeutic effect of the respective electrostimulation of the heart, such as cardiac resynchronization therapy (CRT) or multi-site LV electrostimulation therapy.

In an example, a plurality of signal metrics can be respectively generated using the cardiac electrical signals and the cardiac mechanical signals. The signal metrics can include electrical signal metrics, mechanical signal metrics, or electromechanical metrics indicative of electromechanical coupling of the heart. Examples of the electrical signal metrics can include: intensities (such as amplitudes) and timing of P wave, Q wave, R wave, QRS complex, or T wave of an ECG; timing of sensed activation of RA, RV, and LV obtained from the intracardiac EGMs; QRS width; electrical delay of a chamber of the heart such as LV electrical delay; interventricular conduction delay measured as the delay between LV activation to RV activation (LV-RV) delay; intraventricular delay; Q wave to left ventricle activation (Q-LV) interval, among others. Examples of mechanical signal metrics can include: intensity of a HS components such as S1, S2, S3, or S4 heart sounds; mechanical delay such as time intervals indicative of systole or diastole; pressures inside a heart chamber; end-systolic volume; or end-diastolic volume; among others. Examples of the electromechanical metrics can include a pre-ejection period (PEP) such as measured as an interval from the onset of the QRS to the S1 heart sound, a systolic timing interval (STI) such as measured as an interval between an onset of the QRS and the S2 heart sound, or a diastolic timing interval (DTI) such as measured as an interval from S2 heart sound to the next Q wave, PEP/LVET ratio, STI/DTI ratio, STI/CL ratio, DTI/CL ratio, among others.

At least some of the electrical signal metrics, mechanical signal metrics, or electromechanical metrics can be used to generate a composite score, which can be a numerical or categorical value indicating the therapeutic efficacy of the cardiac stimulation. The composite score can be computed using a linear or non-linear fusion algorithm, including a decision tree, voting method, weighted average, and a neural network, among others.

At 640, a battery longevity indicator can be generated, such as by using one or more parameters indicative of power consumption. These parameters include polarity and number of electrodes that form a stimulation vector, lead impedance, capture threshold indicative of minimum amount of energy required to generating a propagating cardiac depolarization, mode or sequence of electrostimulation that affects the "ON" time for delivery of electrostimulation, electrostimulation intensity or electrostimulation waveform parameters including pulse amplitude, pulse width, pulse shape, frequency, or duty cycle, among others.

At 650, at least some of the candidate electrostimulation vectors can be ranked using the cardiac stimulation efficacy indicators corresponding to the respective candidate electrostimulation vectors, and the battery longevity indicators when the programmable electrostimulator circuit respectively operates according to the plurality of candidate electrostimulation vectors. In an example, the candidate electrostimulation vectors can be ranked using a multi-level ranking method. For example, first ranked vectors can first be generated according to a first specified order of first indicators, such as a descending order of the cardiac stimulation efficacy indicators. Then, second ranked vectors can be generate by ranking at least a portion of the first ranked vectors according to a second specified order of second indicators, such as a descending order of the battery longevity indicators. The portion of the first ranked vectors have corresponding first indicators that meet a specified condition, such as the corresponding first indicators have identical values or fall within a specified range. In another example, the ranking can be performed using an input from a system user, such as a clinician, who can choose from a set of predetermined options of factors (e.g., the electrostimulation efficacy indicators and the battery longevity indicators) and ranking methods (e.g., ascending or descending order for each factor, or a sequence used for multi-level ranking) for prioritizing the candidate electrostimulation vectors.

At 660, the ranked candidate electrostimulation vectors can be utilized in one or more optional actions including information presentation, electrostimulation vector recommendation, therapy programming, or automatic or confirmatory therapy delivery. At 661, information including the ranked electrostimulation vectors, the respective cardiac stimulation efficacy indicators, and the battery longevity indicators can be displayed on a user interface unit. Such information can be presented in a textual, tabular, or graphical format such as a table, a chart, or a diagram, among others. Additionally or alternatively, at 662, a user's selection from the ranked electrostimulation vectors can be received, such as via a user input device. The user can program delivery of the electrostimulation to one or more sites of the heart using the selected one or more vectors. Additionally or alternatively, at 663, at least one electrostimulation vector can be automatically selected from the ranked electrostimulation vectors, and electrostimulation can be delivered using the selected electrostimulation vector. In an example, two or more vectors from the ranked LV electrostimulation vectors can be automatically or manually selected, and multi-site LV electrostimulation using respective two or more LV electrostimulation vectors can be delivered within a cardiac cycle, either simultaneously or asynchronously separated by a specified temporal offset less than a sensed or paced time interval value of the cardiac cycle.

In some examples, the method 600 can further include detecting a complication indicator indicating non-cardiac activation produced by the electrostimulation to the heart using a specified electrostimulation vector. The complication indicator can include one or more indications of extra-cardiac stimulation or non-cardiac muscle stimulation such as stimulation of skeletal muscle, diaphragm, phrenic nerve activation, unintended nerve stimulation, anodal cardiac stimulation, or any other parameters that do not support intended cardiac therapeutic effect. For example, presence of phrenic nerve activation can be detected using an accelerometer for sensing diagram contraction during the cardiac electrostimulation. The complication indicators can include one or more parameters including phrenic nerve stimulation threshold ($PNS_T$) representing minimum stimulation energy or voltage sufficient to elicit phrenic nerve activation, or a safety margin for phrenic nerve activation such as determined as a relationship between the $PNS_T$ and the cardiac capture threshold.

The complication indicators can be used together with the stimulation efficacy indicators and the battery longevity indicators to rank at least some of the plurality of candidate electrostimulation vectors at 650. Absence of phrenic nerve activation, a higher $PNS_T$, or a larger safety margin, is generally preferred over the presence of phrenic nerve activation, a lower $PNS_T$, or a smaller safety margin. In an example of using the method 600 to rank a plurality of LV electrostimulation vectors for use in CRT therapy or multi-site LV electrostimulation therapy, a multi-level ranking of the LV electrostimulation vectors at 650 can include generating the first ranked vectors according to a descending order of the cardiac stimulation efficacy indicators, generating the second ranked vectors according to a descending order of the PNS indicators such as safety margins between the $PNS_T$ and the cardiac stimulation threshold, and generating the third ranked vectors according to a descending order of the battery longevity indicators. The ranked LV electrostimulation vectors can be displayed at 661, and at least one LV electrostimulation vector (such as the one on the top of the ranked list) can be selected at 662, and electrostimulation can be delivered using the selected LV electrostimulation vectors for restoring or improving cardiac function in HF.

Figure 7:
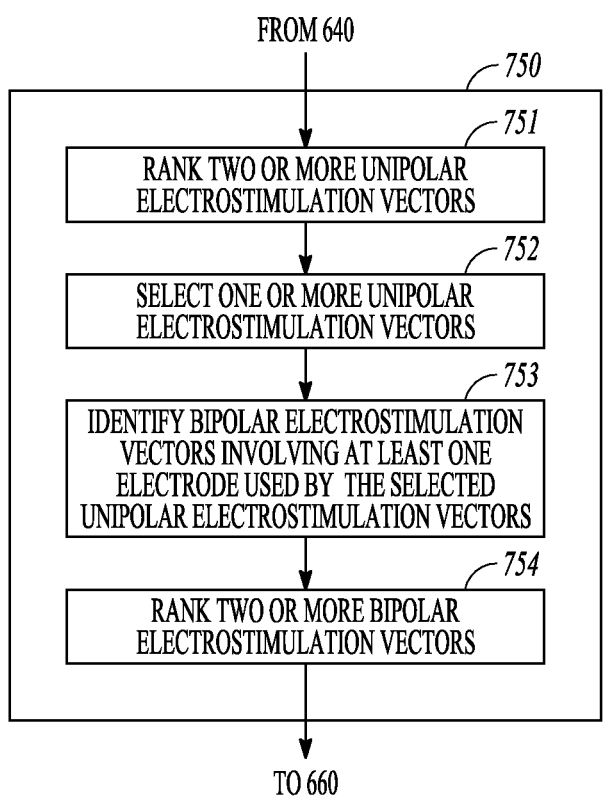
FIG. 7 illustrates generally an example of a method for ranking a plurality of candidate electrostimulation vectors.

FIG. 7 illustrates generally an example of a method 750 for ranking a plurality of candidate electrostimulation vectors. The method 750, which can be a specific embodiment of the pacing vector ranking method at step 650 of FIG. 6, can be used to select at least one unipolar electrostimulation vector from a plurality of unipolar electrostimulation vectors, and to select at least one bipolar electrostimulation vector from a plurality of bipolar electrostimulation vectors.

Each unipolar electrostimulation vector can involve an electrode positioned at or near a target stimulation site of the heart such as an electrode on one of the leads 108A-C, and a return electrode such as the IMD can 112. Each bipolar electrostimulation vector can involve two electrodes, such as on one or more of the leads 108A-C. In an example of ranking and selecting LV electrostimulation vectors, a unipolar LV electrostimulation vector can involve a cathode being an LV electrode, such as one of the electrodes 161-164 along the LV lead 108C; while a bipolar LV electrostimulation vector can involve both a cathode and an anode selected from the LV electrodes, such as the electrodes 161-164 along the LV lead 108C.

At 751, two or more unipolar electrostimulation vectors can be ranked, such as by using the cardiac electrostimulation efficacy indicators and the battery longevity indicators, or additionally using the electromechanical indicators, as discussed above with respect to step 650 of FIG. 6. At 752, one or more unipolar electrostimulation vectors can be selected from the ranked unipolar vectors. Then, at 753, one or more bipolar LV electrostimulation vectors each of which involves a cathode or an anode used by the selected unipolar LV electrostimulation vector are identified. At 754, the identified bipolar LV electrostimulation vectors can be ranked using the cardiac electrostimulation efficacy indicators and the battery longevity indicators, or additionally using the electromechanical indicators, as discussed above with respect to step 650 of FIG. 6. In an example of ranking and selecting LV electrostimulation vectors, a bipolar LV electrostimulation vector with both the cathode and the anode being also used by the selected unipolar LV electrostimulation vectors can be ranked at a higher priority than a bipolar LV electrostimulation vector with only one electrode (either the anode or the cathode) being also used by the selected unipolar LV electrostimulation vectors. The ranked unipolar electrostimulation vectors produced at step 751 and the ranked bipolar electrostimulation vectors produced at step 754 can then be utilized in one or more optional actions at step 660, including information presentation, electrostimulation vector recommendation, therapy programming, or automatic or confirmatory therapy delivery.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for evaluating a plurality of candidate electrostimulation vectors for use in therapeutic stimulation of a heart, the system comprising:
    a programmable electrostimulator circuit, powered by a battery, configured to deliver electrostimulation to at least one site of the heart using a specified electrostimulation vector;
    a physiologic sensor circuit configured to sense one or more physiologic signals;
    a processor circuit, configured to compute a composite efficacy score using at least two cardiac electrical or mechanical signal metrics generated from the sensed one or more physiologic signals, and to generate at least (1) a cardiac stimulation efficacy indicator using the computed composite stimulation efficiency score and (2) a battery longevity indicator, the cardiac stimulation efficacy indicator including a numerical or categorical value indicating a therapeutic effect of the electrostimulation of the heart using the specified electrostimulation vector, the battery longevity indicator including a numerical or categorical value indicating a battery status when the programmable electrostimulator circuit operates according to the specified electrostimulation vector;
    an electrostimulation vector assessment circuit, included in or communicatively coupled to the processor circuit, configured to:
        for the plurality of candidate electrostimulation vectors, receive respective cardiac stimulation efficacy indicators and respective battery longevity indicators; and
        produce a rankable set of at least some of the plurality of candidate electrostimulation vectors, the rankable set operatively rankable according to the respective cardiac stimulation efficacy indicators and the respective battery longevity indicators.

2. The system of claim 1, wherein the electrostimulation vector assessment circuit is configured to rank at least some of the plurality of candidate electrostimulation vectors, the ranking including:
    generating first ranked vectors by ranking the at least some of the plurality of candidate electrostimulation vectors according to a first specified order of first indicators; and
    generating second ranked vectors by ranking at least a portion of the first ranked vectors according to a second specified order of second indicators, the portion of the first ranked vectors having corresponding first indicators meeting a specified condition;
    wherein the first indicators are one, and the second indicators are the other, of the respective cardiac stimulation efficacy indicators or the respective battery longevity indicators.

3. The system of claim 2, wherein the electrostimulation vector assessment circuit is configured to generate the first ranked vectors according to a descending order of the respective cardiac stimulation efficacy indicators, and to generate the second ranked vectors according to a descending order of the respective battery longevity indicators.

4. The system of claim 1, wherein the processor circuit is further configured to generate a complication indicator indicating non-cardiac activation produced by an electrostimulation using the specified electrostimulation vector to the heart, wherein the electrostimulation vector assessment circuit is further configured to:

for the plurality of candidate electrostimulation vectors, receive respective complication indicators; and rank at least some of the plurality of candidate electrostimulation vectors further using the complication indicators.

5. The system of claim 4, wherein the respective complication indicators respectively include information about phrenic nerve activation, the information including at least one of presence or absence of phrenic nerve activation, a phrenic nerve stimulation threshold ($PNS_T$) indicative of minimum electrostimulation intensity sufficient to elicit phrenic nerve activation, or a safety margin indicative of a relationship between the $PNS_T$ and a cardiac capture threshold.

6. The system of claim 5, wherein the electrostimulation vector assessment circuit is configured to rank at least some the plurality of candidate electrostimulation vectors, the ranking including:

generating first ranked vectors by ranking the at least some of the plurality of candidate electrostimulation vectors according to a first specified order of first indicators;

generating second ranked vectors by ranking at least a portion of the first ranked vectors according to a second specified order of second indicators, the portion of the first ranked vectors having corresponding first indicators meeting a specified condition; and generating third ranked vectors by ranking at least a portion of the second ranked vectors according to a third specified order of third indicators, the portion of the second ranked vectors having corresponding second indicators meeting a specified condition;

wherein the first, second, and third indicators are mutually different ones of the respective cardiac stimulation efficacy indicators, the respective battery longevity indicators, and the respective complication indicators.

7. The system of claim 1, further comprising a user interface unit configured to:

display the ranked electrostimulation vectors, the corresponding respective cardiac stimulation efficacy indicators, and the corresponding battery longevity indicators; and receive a user input, including selecting at least one electrostimulation vector from the ranked electrostimulation vectors and programming the programmable electrostimulator circuit to deliver electrostimulation to the heart using the selected at least one electrostimulation vector.

8. The system of claim 1, comprising one or more left ventricle (LV) electrodes removably and respectively positionable at an LV of the heart, wherein the programmable electrostimulator circuit is configured to be electrically coupled to the one or more LV electrodes and configured to deliver LV electrostimulation using a specified LV electrostimulation vector involving at least one of the LV electrodes.

9. The system of claim 8, wherein the plurality of candidate electrostimulation vectors include two or more unipolar LV electrostimulation vectors and two or more bipolar LV electrostimulation vectors, and the electrostimulation vector assessment circuit is configured to:

rank the two or more unipolar LV electrostimulation vectors using first cardiac stimulation efficacy indicators and first battery longevity indicators in response to LV electrostimulation using the two or more unipolar LV electrostimulation vectors;

select, automatically or based on a user input, one or more unipolar LV electrostimulation vectors from the ranked unipolar LV electrostimulation vectors;

identify, from the two or more bipolar LV electrostimulation vectors, bipolar LV electrostimulation vectors each involving at least one electrode used by the selected unipolar LV electrostimulation vectors; and rank the identified bipolar LV electrostimulation vectors using second cardiac stimulation efficacy indicators and second battery longevity indicators in response to LV electrostimulation using the identified bipolar LV electrostimulation vectors.

10. The system of claim 8, wherein:

the electrostimulation vector assessment circuit is configured to select from the ranked LV electrostimulation vectors, automatically or based on a user input, at least first and second LV electrostimulation vectors, and;

the programmable electrostimulator circuit is configured to, during the same cardiac cycle, deliver a first LV electrostimulation using the first selected LV electrostimulation vector and deliver a second LV electrostimulation using the second selected LV electrostimulation vector.

11. The system of claim 1, wherein:

the physiologic sensor circuit is configured to sense at least a cardiac electrical signal and a cardiac mechanical signal in response to the electrostimulation of the one or more sites of the heart according a specified electrostimulation vector; and the processor circuit is configured to generate one or more electrical signal metrics and one or more mechanical signal metrics using the cardiac electrical signal and the cardiac mechanical signal, and generate the cardiac stimulation efficacy indicator using the one or more electrical signal metrics and the one or more mechanical signal metrics.

12. The system of claim 1, wherein the processor circuit is configured to generate the battery longevity indicator using one or more of cardiac capture threshold, electrostimulation intensity, electrostimulation waveform, lead impedance, or number of electrodes involved in the specified electrostimulation vector.

13. A method for evaluating a plurality of candidate electrostimulation vectors for use in therapeutic stimulation of a heart, comprising:

delivering respective electrostimulation to at least one site of the heart using the plurality of candidate electrostimulation vectors;

sensing respective one or more physiologic signals in response to the delivery of the respective electrostimulation;

computing respective composite efficacy scores using at least two cardiac electrical or mechanical signal metrics generated from the sensed respective one or more physiologic signals;

generating (1) respective cardiac stimulation efficacy indicators using the computed respective composite efficacy scores and (2) respective battery longevity indicators, the respective cardiac stimulation efficacy indicators each including a numerical or categorical value indicating a therapeutic effect of the respective electrostimulation of the heart, the respective battery longevity indicators each including a numerical or categorical value indicating a battery status when the programmable electrostimulator circuit respectively operates according to one of the plurality of electrostimulation vectors;

ranking at least some of the plurality of candidate electrostimulation vectors using the respective cardiac stimulation efficacy indicators and the respective battery longevity indicators.

14. The method of claim 13, wherein ranking at least some of the plurality of candidate electrostimulation vectors includes:
generating first ranked vectors by ranking the at least some of the plurality of candidate electrostimulation vectors according to a first specified order of first indicators; and
generating second ranked vectors by ranking at least a portion of the first ranked vectors according to a second specified order of second indicators, the portion of the first ranked vectors having corresponding first indicators meeting a specified condition;
wherein the first indicators are one, and the second indicators being the other, of the respective cardiac stimulation efficacy indicators or the respective battery longevity indicators.

15. The method of claim 14, wherein ranking at least some of the plurality of candidate electrostimulation vectors includes generating the first ranked vectors according to a descending order of the respective cardiac stimulation efficacy indicators, and generating the second ranked vectors according to a descending order of the respective battery longevity indicators.

16. The method of claim 14, further comprising, in response to the electrostimulation respectively delivered using the plurality of candidate electrostimulation vectors, generating respective complication indicators each indicating non-cardiac activation produced by the electrostimulation, wherein ranking the candidate electrostimulation vectors includes ranking at least some of the plurality of candidate electrostimulation vectors further using the respective complication indicators,
wherein the respective complication indicators respectively include information about phrenic nerve activation, the information including at least one of presence or absence of phrenic nerve activation, a phrenic nerve stimulation threshold ($PNS_T$) indicative of minimum electrostimulation intensity sufficient to elicit phrenic nerve activation, or a safety margin indicative of a relationship between the $PNS_T$ and a cardiac capture threshold.

17. The method of claim 16, wherein ranking the candidate electrostimulation vectors includes:
generating first ranked vectors by ranking the at least some of the plurality of candidate electrostimulation vectors according to a first specified order of first indicators;
generating second ranked vectors by ranking at least a portion of the first ranked vectors according to a second specified order of second indicators, the portion of the first ranked vectors having corresponding first indicators meeting a specified condition; and
generating third ranked vectors by ranking at least a portion of the second ranked vectors according to a third specified order of third indicators, the portion of the second ranked vectors having corresponding second indicators meeting a specified condition;
wherein the first, second, and third indicators are mutually different ones of the respective cardiac stimulation efficacy indicators, the respective battery longevity indicators, and the respective complication indicators.

18. The method of claim 13, further comprising:
displaying in a user interface unit the ranked electrostimulation vectors, the corresponding respective cardiac stimulation efficacy indicators, and the corresponding respective battery longevity indicators;
selecting, automatically or based on a user input, at least one electrostimulation vector from the ranked electrostimulation vectors; and
delivering electrostimulation to the heart using the selected at least one electrostimulation vector.

19. The method of claim 13, wherein delivering the electrostimulation includes delivering left ventricular (LV) pacing pulses to one or more LV sites using a plurality of candidate LV electrostimulation vectors including two or more unipolar LV electrostimulation vectors and two or more bipolar LV electrostimulation vectors, wherein ranking the plurality of candidate electrostimulation vectors includes:
ranking the two or more unipolar LV electrostimulation vectors using first cardiac stimulation efficacy indicators and first battery longevity indicators in response to LV electrostimulation using the two or more unipolar LV electrostimulation vectors;
selecting, automatically or based on a user input, one or more unipolar LV electrostimulation vectors from the ranked unipolar LV electrostimulation vectors;
identifying, from the two or more bipolar LV electrostimulation vectors, bipolar LV electrostimulation vectors each involving at least one electrode used by the selected unipolar LV electrostimulation vectors; and
ranking the identified bipolar LV electrostimulation vectors using second cardiac stimulation efficacy indicators and second battery longevity indicators in response to LV electrostimulation using the identified bipolar LV electrostimulation vectors.

20. The method of claim 13, wherein:
generating the respective cardiac stimulation efficacy indicators includes generating one or more electrical signal metrics and one or more mechanical signal metrics, and generating the cardiac stimulation efficacy indicator using a linear or nonlinear combination of at least some of the one or more electrical signal metrics and the one or more mechanical signal metrics; and
generating the respective battery longevity indicators includes generating the respective battery longevity indicators using one or more of cardiac capture threshold, electrostimulation intensity, electrostimulation waveform, lead impedance, or number of electrodes involved in the specified electrostimulation vector.

* * * * *